(12) United States Patent
Lee et al.

(10) Patent No.: US 8,680,039 B2
(45) Date of Patent: Mar. 25, 2014

(54) FABRIC SOFTENER AND PREPARATION METHOD THEREOF

(71) Applicant: Sunjin Chemical Co., Ltd., Gyeonggi-Do (KR)

(72) Inventors: Sang-Ho Lee, Gyeonggi-Do (KR); Han-Song Chu, Gyeonggi-Do (KR); Jae-Young Choi, Gyeonggi-Do (KR); Se-Kyu Hwang, Gyeonggi-Do (KR)

(73) Assignee: Sunjin Chemical Co., Ltd., Ansan, Gyeonggi-Do (KR)

( * ) Notice: Subject to any disclaimer, the term of this patent is extended or adjusted under 35 U.S.C. 154(b) by 0 days.

(21) Appl. No.: 13/754,118

(22) Filed: Jan. 30, 2013

(65) Prior Publication Data

US 2013/0143789 A1     Jun. 6, 2013

Related U.S. Application Data

(63) Continuation of application No. PCT/KR2011/002021, filed on Mar. 24, 2011.

(30) Foreign Application Priority Data

Aug. 3, 2010   (KR) .................. 10-2010-0074946
Mar. 22, 2011  (KR) .................. 10-2011-0025325

(51) Int. Cl.
   *C11D 1/645*     (2006.01)

(52) U.S. Cl.
   USPC ........................................ 510/504

(58) Field of Classification Search
   USPC ........................................ 510/504
   See application file for complete search history.

(56) References Cited

U.S. PATENT DOCUMENTS

| | | | | |
|---|---|---|---|---|
| 3,915,867 A * | 10/1975 | Kang et al. | ..................... | 510/525 |
| 5,705,663 A * | 1/1998 | Brock et al. | ................... | 554/110 |
| 5,830,845 A * | 11/1998 | Trinh et al. | .................... | 510/504 |
| 6,906,025 B2 * | 6/2005 | Levinson | ...................... | 510/520 |
| 2001/0036909 A1 * | 11/2001 | Levinson | ...................... | 510/327 |

FOREIGN PATENT DOCUMENTS

| | | | |
|---|---|---|---|
| EP | 284036 | * | 9/1988 |
| EP | 580527 | * | 1/1994 |

* cited by examiner

*Primary Examiner* — John Hardee
(74) *Attorney, Agent, or Firm* — Edwards Wildman Palmer LLP

(57) ABSTRACT

The present invention relates to a method of preparing a fabric softener and to a fabric softener prepared thereby, and more particularly, to a method of preparing a fabric softener containing an esterquat by performing a two-step transesterification reaction on oil and tertiary hydroxyalkyl amine at a low temperature in a high vacuum state under specific conditions, and then quaternizing the resultant product. The method of preparing a fabric softener containing an esterquat according to the present invention can reduce the content of unconverted glyceride, glyceryl ester, or a mixture thereof, and can provide a fabric softener with excellent long-term stability.

12 Claims, No Drawings

FABRIC SOFTENER AND PREPARATION METHOD THEREOF

CROSS-REFERENCE TO RELATED APPLICATIONS

This application is a continuation of International Application No. PCT/KR2011/002021 filed on Mar. 24, 2011, which claims priority to Korean Application No. 10-2010-0074946 filed on Aug. 3, 2010 and Korean Application No. 10-2011-0025325 filed on Mar. 22, 2011, which applications are incorporated herein by reference.

TECHNICAL FIELD

This invention relates to a method of preparing a fabric softener wherein an esterquat is prepared by performing the transesterification reaction of a fatty acid containing oil and the quaternization thereof and to a fabric softener prepared thereby, and the method of preparing a fabric softener according to the invention has an advantage in that the content of unconverted glyceride, glyceryl ester, or a mixture thereof is low.

BACKGROUND ART

Fabric softeners, as finishing agents to provide softness to fabrics after laundry, usually provide antistatic effects as well as softness with regard to fabrics.

Previously, dimethyl dialkyl ammonium chloride (DDAC) was widely used as a fabric softener but after that, through quaternary ammonium salts of amino amine, imidazoline, imidazoline ester-type fabric softeners, there are currently being used most throughout the world cationic surfactant-containing fabric softeners which are prepared in the form of an esterquat by quaternizing ester compounds induced from fatty acids and tertiary amines.

However, since the fatty acids to be used in preparing the above fabric softeners are expensive, there have been lately developed methods of preparing fabric softeners from vegetable oils that replace expensive fatty acids in order to reduce manufacturing costs.

As methods of preparing fabric softeners by using oils, U.S. Pat. No. 5,869,716 discloses a method of preparing a fabric softener by reacting oil and hydroxyfunctionalized tertiary amine in the presence of a catalyst such as an alkali metal borohydride or an alkaline earth metal borohydride and then, reacting the obtained product with a quaternizing agent. U.S. Pat. No. 6,906,025 and U.S. Pat. No. 7,001,879 disclose a method of preparing a fabric softener by the transesterification reaction of oils in the form of triglyceride and amines in the presence of sodium borohydride, or sodium borohydride and calcium hydroxide. However, the methods of preparing cationic fabric softeners directly from oils as in those methods had high oil content in the form of unconverted glycerides, or resulted in fabric softeners having poor colors.

For this, there have been suggested methods for lowering the content of unconverted triglyceride and improving color by using strong alkali and borohydride catalysts, but these methods still result in high unreacted triglyceride content, and bad colors and odors.

Further, Korean Patent No. 854099 and No. 861699 each discloses a method of preparing an esterquat by performing the transesterification reaction of oils and tertiary amines at a high temperature under nitrogen atmosphere in the presence of alkali catalysts or titanium alkoxide catalysts, and then quaternizing the resultant product. However, the above method has a high reaction temperature and long reaction time due to a low solubility against reactants. Furthermore, since stearic acid is added to the oils in the transesterification reaction at a high temperature under nitrogen atmosphere, or a partially hydrogenated oil form is used by performing hydrogenation with regard to the oils prior to the transesterification reaction, it still has drawbacks that color enhancement effects are low and the content of oils in the form of glycerin and unconverted glycerides is high. As a result, for the color improvement of the fabric softeners, the use of a decolorant which causes skin trouble and irritation is essential after the reaction with quaternizing agents.

SUMMARY

In order to solve the problems of the prior arts as described in the above, it is an object of the invention to provide a method of preparing a fabric softener containing an esterquat, which can reduce the content of glycerin and glycerides among the final materials obtained after transesterification reaction and quaternization reaction and has excellent long-term stability, by performing a two-step transesterification reaction at a low temperature in a high vacuum state to block the inflow of oxygen or air and by removing glycerin to the outside of a reactor.

It is another object of the invention to provide a fabric softener which is prepared by the above method and has the content of glycerin and glycerides in 5 wt. % or less without separate removal process of glycerin and glycerides.

The invention provides a method of preparing a fabric softener containing an esterquat of formula 1:

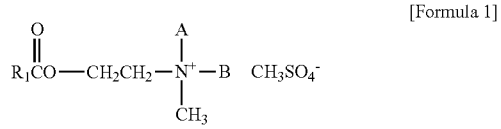

[Formula 1]

wherein A and B are each independently $CH_2CH_2OH$ or $CH_2CH_2OCR_2$, and $R_1$ and $R_2$ are each independently selected from the group consisting of a linear or branched alkyl group and alkenyl group of $C_{11}$-$C_{21}$, and a combination group thereof, by performing a first transesterification reaction of a fatty acid containing oil and a tertiary hydroxyalkylamine at a temperature of 110-130° C. under the pressure condition of 50 mmHg or less and performing a second transesterification reaction at a temperature of 130-160° C. which is increased at a point where 40-60% of the oil is converted into a reactant to prepare a fatty acid hydroxyalkylamine ester; and by reacting the thus prepared fatty acid hydroxyalkylamine ester with a quaternizing agent in a solvent.

Further, the invention provides a fabric softener prepared by the above method comprising 20 to 90 wt. % of an esterquat of the above formula 1; 0.001 to 5 wt. % of glycerin, glycerylester, or a mixture thereof; and a residual amount of a solvent.

When a fabric softener containing an esterquat is prepared by the method according to the present invention, the content of unconverted glyceride, glycerylester or a combination thereof can be reduced and a fabric softener with excellent long-term stability can be produced.

DETAILED DESCRIPTION

In general, when fabric softeners containing esterquats are prepared, fatty acid hydroxyalkylamine esters are prepared as the results of the transesterification reaction of tertiary hydroxyalkylamines and fatty acid parts of oils and at the same time, glycerin, glyceride or a mixture thereof is also generated as by-products, depending on the progress levels the transesterification reaction. In particular, in case that fatty acids of vegetable oils and tertiary hydroxyalkylamines are all converted into fatty acid hydroxyalkylamine esters by transesterification reaction, partial glycerins remain as a residual material, and in case that the fatty acids of vegetable oils are partially converted into fatty acid hydroxyalkylamine esters by transesterification reaction, compounds in the form of a glycerylester such as a triglyceride remain as a residual material, depending on the number of the fatty acids still remaining in the vegetable oils that are not being unconverted.

For this, the invention is intended to prepare a fabric softener capable of reducing the residues of glycerin, glyceride, or a mixture thereof, having excellent color improvement effects without requiring the input of a decolorant which causes skin trouble and irritation, and improving the softness of fabrics as well as long-term stability, by virtue of a low temperature and a high vacuum reaction in transesterification reaction for the preparation of esterquats.

The method of preparing a fabric softener according to the invention comprises the preparation of a fabric softener containing an esterquat of the formula 1 by performing a first transesterification reaction of a fatty acid containing oil and a tertiary hydroxyalkylamine at a temperature of 110-130° C. under the pressure condition of 50 mmHg or less and performing a second transesterification reaction at a temperature of 130-160° C. which is increased at a point where 40-60% of the oil is converted into a reactant to prepare a fatty acid hydroxyalkylamine ester; and by reacting the thus prepared fatty acid hydroxyalkylamine ester with a quaternizing agent in a solvent.

In one embodiment of the invention, the transesterification reaction and the quaternization reaction may be performed in a closed reactor to which a reduced pressure pump and a glycerin reservoir are connected. For example, the closed reactor is connected with the glycerin reservoir through a pipe and the glycerin reservoir is connected with the vacuum pump, and a gaseous glycerin inside the reactor is discharged into the outside of the reactor via the connected pipe and the discharged glycerin is transferred to the connected glycerin reservoir, being changed into its liquid phase while it is passing through a condenser. Under specific temperature and pressure conditions, glycerin is vaporized and then discharged via the pipe connected to the reactor under a low pressure. When the temperature and pressure of the reactor are considered, it is desirable that glycerin is discharged outside the reactor under second reaction conditions of the transesterification reactions. Through such processes, the content of glycerin and glyceride within the reactants becomes very low after the transesterification reaction and accordingly, the content of glycerin and glyceride in the finally produced fabric softener is so low that an excellent fabric softener can be obtained. Also, it is very economical in that the recovered glycerin can be further used as a solvent for quaternization reaction.

Hereafter, the process will be explained in each step in detail.

The transesterification reaction in the present invention is a step of preparing a fatty acid hydroxyl alkylamine ester by the transesterification reaction of oil and a tertiary hydroxyalkylamine. More particularly, this process is to prepare a fatty acid hydroxyl alkylamine ester by performing a first transesterification reaction of a fatty acid containing oil and a tertiary hydroxyalkylamine at a temperature of 110-130° C. under the pressure condition of 50 mmHg or less and performing a second transesterification reaction at a temperature of 130-160° C. which is increased.

Preferably, it is desirable to use triglyceride containing many substituents in the form of fatty acids, such as a palm oil, palm stearin oil, palm olein oil, coconut oil, olive oil or soybean oil because as more fatty acids are contained in the oils, the softness of fabrics can be improved in the preparation of esterquats.

The tertiary hydroxyalkyl amines available in the invention may include diethanol/methylamine, 1,2-dihydroxypropyl dimethylamine, triethanolamine and so on and they may be used alone or in a combination thereof.

The fatty acid containing vegetable oils and the tertiary hydroxyalkylamines may be used preferably in a reaction molar ratio of 1.5:1 to 2.5:1 of the fatty acid of the vegetable oils and the tertiary hydroxyalkylamine.

The catalysts available in the present invention may include sodium alkoxide catalysts such as sodium methoxide, sodium ethoxide, sodium propoxide, or sodium butoxide; titanium oxide catalysts such as titanium oxide; zinc oxide catalysts such as zinc oxide; alkali catalysts such as silica sodium hydroxide, potassium hydroxide, calcium hydroxide, anhydrous sodium carbonate, etc.; or sodium hypochlorite, etc., and they may be used alone or in a combination thereof.

Of them, it is preferable to use titanium oxide catalysts or zinc oxide catalysts because they are environment-friendly and harmless to humans, have excellent reactivity so that they can rapidly hydrolyze with only slight moisture from air or solvents to form hydroxides, and they can also form high activity photocatalysts such as a titanium oxide by heat drying at a relatively low temperature so that they can add functions as photocatalysts such as antibacterial functions and bad odor elimination to the fabric softeners containing them. More preferably, the catalysts may include at least one main catalyst selected from the group consisting of sodium alkoxide catalysts, titanium oxide catalysts, zinc oxide catalysts, silica and alkali catalysts, and a sodium hypochlorite anticatalyst.

The catalyst may be used preferably in an amount of 0.03 to 0.1 parts by weight with regard to a total of 100 parts by weight of the fatty acid containing oil and the tertiary hydroxyalkylamine.

More preferably, the alkali catalyst and sodium hypochlorite may be used in an amount of 0.03 to 0.1 parts by weight, respectively with regard to a total of 100 parts by weight of the fatty acid containing oil and the tertiary hydroxyalkylamine, for excellent color improvement effects during the transesterification reaction.

In the transesterification reaction, the first transesterification reaction may be carried out for 3 to 10 hours in a temperature range of 110-130° C. and the second transesterification reaction may be carried out for 1 to 13 hours in a temperature range of 130-160° C. More particularly, when the transesterification reaction is carried out using no catalysts, the first transesterification may be carried out for 6 to 10 hours and the second transesterification reaction may be carried out for 5 to 13 hours, and when the catalysts are used, the first transesterification may be carried out for 3 to 7 hours and the second transesterification reaction may be carried out for 5 to 13 hours Also, the pressure conditions for the transesterification reaction may be 0-50 mmHg and preferably, the pressure of the second transesterification reaction may be lower than the pressure of the first transesterification reaction. If the reaction pressure of the second transesterification reaction is lower than that of the first transesterification reaction, glycerin may be recovered well. Preferably, the pressure of the first transesterification reaction in the invention may be 10 to 50 mmHg, more preferably 10 to 20 mmHg, and the pressure of the second transesterification reaction may be 0 to 10 mmHg, more preferably 0 to 5 mmHg. If they deviate from the above temperature ranges and vacuum pressure ranges, it may result in poor color due to a large content of unconverted triglyceride oils and also cause a decrease in long-term stability.

The conversion into the second transesterification reaction from the first transesterification reaction by increasing the reaction temperature may be carried out at a point where 40 to 60% of the oil is converted into a reactant, and the conversion rate of the oil may be measured by the amount of the produced glycerin. For example, when 60% of the oil is converted into the reactant, the content of the produced glycerin may be 5 to 7 parts by weight with regard to 100 parts by weight of the initially injected oil. Also, the completion of the second transesterification reaction may be carried out at a point where 98% or more of the oil is converted into the reactant, and the conversion rate of the oil may be measured by the amount of the produced glycerin. If the oil is reacted in less than 40% for the first transesterification reaction, unreacted triglyceride materials become abundant, and if the oil is reacted in 60% or more, the color of the product is deteriorated.

The method of preparing a fabric softener in accordance with the invention has an advantage in that the content of an unconverted glyceride, glycerylester or a mixture thereof is low. In particular, the invention is a method where at least one material selected from the group consisting of the glycerin and glycerides represented by formulae 2 to 6 below is 0.001 to 5% by weight.

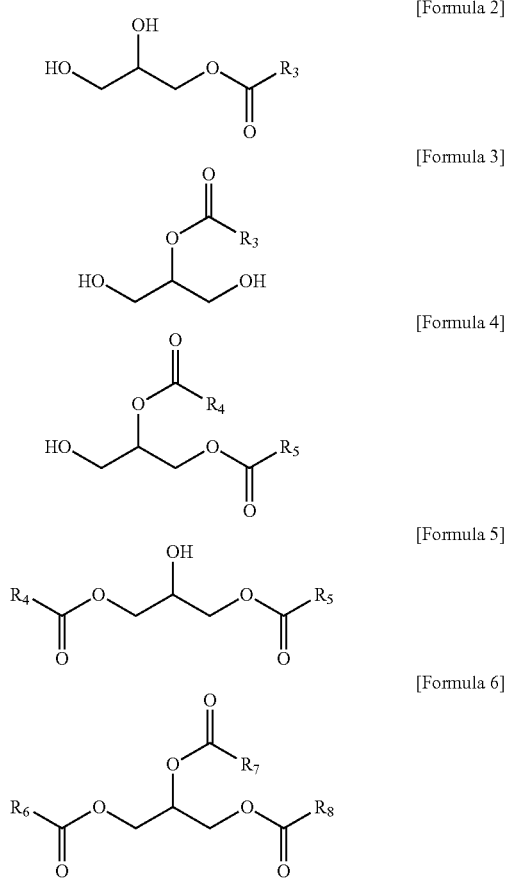

[Formula 2]
[Formula 3]
[Formula 4]
[Formula 5]
[Formula 6]

In the above formulae 2 to 6, $R_3$ to $R_8$ are each independently a linear or branched alkyl group or alkenyl group of $C_{11}$-$C_{21}$.

The quaternization reaction is a step of obtaining a fabric softener containing an esterquat by reacting the fatty acid hydroxyalkylamine ester obtained from the transesterification reaction with a quaternizing agent in a solvent.

The quaternizing agents available in the present invention may include alkyl halides such as methyl chloride; dialkyl phosphates such as dimethyl sulfate; dialkyl carbonates such as dimethyl carbonate and diethyl carbonate, etc., and they may be used alone or in a combination thereof.

The fatty acid hydroxyalkylamine ester and the quaternizing agent may be preferably included in a reaction molar ratio of 1:0.9 to 1:1. If the reaction molar ratio is less than 1:0.9, its emulsibility might be deteriorated due to an increased alkylamine ester, and if it exceeds 1:1, it might cause a problem in human body safety and product stability due to the residues of unreacted quaternizing agent.

The solvent available in the present invention may include lower alcohols having carbon atoms of 1 to 6 such as ethyl alcohol, propyl alcohol, isopropyl alcohol, etc; alkylene glycol having carbon atoms of 1 to 6 such as ethylene glycol, diethylene glycol, propylene glycol, polyethylene glycol, etc.; glycerin and so, and they can be used alone or in a combination thereof.

The solvent may be used preferably in 5 to 30 parts by weight with regard to 100 parts by weight of the fatty acid hydroxyalkylamine.

The quaternization reaction may be carried out for 3 to 10 hours at 35 to 50° C., preferably for 3 to 6 hours at 45 to 50° C.

By the method as described in the above, the fabric softener containing an esterquat of the following formula 1 can be prepared.

[Formula 1]

Wherein A and B are each independently $CH_2CH_2OH$ or $CH_2CH_2OCR_2$, and $R_1$ and $R_2$ are each independently selected from the group consisting of a linear or branched alkyl group and alkenyl group of $C_{11}$-$C_{21}$, and a combination group thereof.

When a fabric softener is prepared by the method according to the present invention, unconverted residues such as glycerin, glycerylester, or a combination thereof can be reduced, the recovered glycerin can be reused as a solvent, it has excellent long-term stability as a fabric softener, and a fabric softener capable of enhancing the softness of fabrics can be readily prepared.

Further, the invention provides a fabric softener containing an esterquat of formula 1 as defined above, prepared by the method as described above.

The fabric softener may include preferably 20-90 wt. % of an esterquat of formula 1, 0.001-5 wt. % of glycerin, glycerylester or a combination thereof; and a residual amount of a solvent. Preferably, the content of the glycerin, glycerylester or combination thereof may be less than 2 wt. %. If the content of the glycerin is higher than that, color stability is deteriorated and it may cause the formation of an oil layer when a fabric softener is prepared.

For better understanding of the present invention, preferred examples follow. The following examples are intended to merely illustrate the invention without limiting the scope of the invention.

EXAMPLES

Example 1

Preparation of Catalyst-Free Fabric Softener (1) Transesterification Reaction

To a four-mouth glass reactor connected with a stirrer, a vacuum pump, a thermometer, a condenser, a reservoir for glycerin to be recovered, and a distillation apparatus were put 350 g of a palm stearin oil and 110 g of a triethanolamine in a mixture thereof and then, under conditions that the speed of the stirrer was set at 300-400 rpm, the pressure of the reactor was set to 10 mmHg by operating the vacuum apparatus, and the temperature of the reaction mixture was increased to 125° C., the first transesterification reaction was carried out for 7 hours at that temperature.

The content of the glycerin within the reactor was measured successively in the interval of 1 hour and as a result of the measurement, at a point where the content of the glycerin was 5.0 to 7.0 parts by weight (oil conversion rate 40-60%) with regard to 100% of the initially injected oil, the temperature was increased to 155° C. and then, the reaction continued for 8 hours. The reaction was terminated at a point where the conversion rate that was successively measured during the reaction process while the reactor pressure was being maintained to 5 mmHg was 98% with regard to the initially injected oil, and it was cooled down to 50° C. or under to obtain 440 g of a fatty acid hydroxyalkylamine ester, and 44 g of glycerin was obtained from the glycerin reservoir connected to the reactor.

The measurement of the glycerin content was performed by GC analysis (TE90 carbon composition analysis). 0.2 g of the specimen from the reactor was put into a 100-ml separative funnel, to which 1 ml of pyridine was added and melted. To the reactants were added 0.2 ml of hexamethyldisilazane (HMDS) and 0.1 ml of trimethylchlorosilane (TMCS) and then, after closed with a lid, it was vigorously shaken and then allowed to stay, followed by the addition of 10 ml of n-hexane and then, it was shaken and allowed to stay. It was washed with a 10% NaCl aqueous solution by 4-5 times until pyridine odor vanished. A hexane layer was dehydrated with an anhydrous $Na_2SO_4$ and filtrated and then GC analysis was performed with the following conditions.

Column: non-polar column 30 m
Inlet Temperature: 300° C.
Detector Temperature: 320° C.
Oven Temperature: 100° C.→10° C./min→320° C.×8 min
(2) Quaternization Reaction To 440 g of the fatty acid hydroxyalkylamine ester obtained in step (1) was added 65 g of isopropylalcohol. Thereafter, 90 g of dimethylsulfate, a quaternizing agent, was slowly added dropwise thereto, followed by quaternization reaction for 3 hours at 45-50° C., and then 40 g of the recovered glycerin was added to prepare 635 g of a fabric softener containing esterquats.

Example 2

With the exception that the reactor pressure was lowered to 10 mmHg in the second transesterification reaction of Example 1, the same method as described in Example 1 was performed to prepare 635 g of a fabric softener containing esterquats.

Example 3

A mixture of 0.7 g of sodium methoxide and 0.4 g of sodium hypochlorite was used as a catalyst to execute the reaction in step 1 of the method of Example 1.

The same method as described in Example 1 was performed to prepare 635 g of a fabric softener containing esterquats.

Example 4

With the exception that 0.7 g of sodium hydroxide and 0.4 g of sodium hypochlorite were mixed in the second transesterification reaction of the transesterification reactions in step 1 in Example 1, the same method as described in Example 1 was performed to prepare 635 g of a fabric softener containing esterquats.

Example 5

With the exception that 0.35 g of sodium methoxide and 0.2 g of titanium oxide were mixed in the second transesterification reaction of the transesterification reactions in step 1 in Example 1, the same method as described in Example 1 was performed to prepare 635 g of a fabric softener containing esterquats.

Example 6

The same method as described in Example 1 was performed for the second transesterification reaction of the transesterification reactions in step 1 in Example 1, and an ethanol was added instead of isopropylalcohol in the quaternization reaction to prepare 635 g of a fabric softener containing esterquats.

Comparative Example 1

Preparation of Fabric Softener by Nitrogen Reaction (1) Transesterification Reaction To a four-mouth glass reactor equipped with a mechanical stirrer, a nitrogen supply apparatus, a thermometer, a condenser, and a distillation apparatus were put 591 g of a palm stearin oil, 170 g of a triethanolamine, 0.4 g of a sodium hydroxide, and 0.4 g of a sodium hypochlorite in a mixture thereof and then, after the speed of the stirrer was set at 300-400 rpm, the temperature of the reaction mixture was increased to 120° C., and nitrogen was added, it was maintained for 5 hours and then, after it was reacted for 3 hours at 170° C. that was increased, it was cooled down to 50° C. or under to obtain 761 g of a fatty acid hydroxyalkylamine ester.

(2) Quaternization Reaction

To the fatty acid hydroxyalkylamine ester obtained in step (1) was added 102 g of isopropylalcohol. Thereafter, 135 g of dimethylsulfate, a quaternizing agent, was slowly added dropwise thereto, followed by quaternization reaction for 2 hours at 50-60° C., to prepare 998 g of esterquats.

Comparative Example 2

Preparation of Fabric Softener by High Temperature Nitrogen Reaction

With the exception that 591 g of a palm stearin oil, 170 g of triethanolamine, 0.4 g of potassium hydroxide, and 0.4 g of sodium hypochlorite were used in a mixture thereof in the first transesterification reaction in Comparative Example 1, the same method as described in Comparative Example 1 was performed to prepare 998 g of a fabric softener containing esterquats.

Comparative Example 3

Preparation of Fabric Softener by High Temperature Nitrogen Reaction

With the exception that 591 g of a palm stearin oil, 170 g of triethanolamine, 0.2 g of sodium methoxide, and 0.4 g of sodium hypochlorite were used in a mixture thereof in the transesterification reaction in step 1 of Comparative Example 1, the same method as described in Comparative Example 1 was performed to prepare 998 g of a fabric softener containing esterquats.

Comparative Example 4

After the reaction for 20 hours under 10 mmHg of the reactor pressure while maintaining the temperature of the reaction mixture at 125° C. for the transesterification reaction of step 1 of Example 1, the same quaternization reaction as in Example 1 was performed to prepare 635 g of a fabric softener containing esterquats.

Experimental Example

Color Measurement of Fabric Softener

In order to see color enhancement effects of the fabric softeners according to the present invention, colors were measured by the following method and evaluated for comparison.

The colors (Gardner) of the fatty acid hydroxyalkylamine esters produced after the transesterification reaction according to Examples 1-6 and Comparative Examples 1-4 were measured using a colourimeter (Lovibond Tintometer PFX195) and Gardner. The results were shown in Table 1 below.

TABLE 1

| Example No. | Color (Gardner) |
| --- | --- |
| Example 1 | 1.7 |
| Example 2 | 2.3 |
| Example 3 | 1.4 |
| Example 4 | 1.8 |
| Example 5 | 1.6 |

TABLE 1-continued

| Example No. | Color (Gardner) |
| --- | --- |
| Example 6 | 1.6 |
| Comparative Example 1 | 3.5 |
| Comparative Example 2 | 3.6 |
| Comparative Example 3 | 3.0 |
| Comparative Example 4 | 3.0 |

As seen in Table 1 above, the fabric softeners of Examples 1-6 prepared by the method of the present invention show Gardner colors of 1.4-2.3 so they are suitable to be used as a fabric softener without decolorants. In contrast, the fabric softeners prepared in Comparative Examples 1-3 prepared at high temperature and under a nitrogen atmosphere and Comparative Example 4 where esterification reaction was performed at a low temperature require color enhancement by the addition of decolorants and thus, problems such as irritation and skin troubles owing to the addition of decolorants are unavoidable.

Experimental Example 2

Content Measurement of Glycerin and Unconverted Glyceride

In order to investigate the contents of glycerin and unconverted glycerides when the fabric softeners were prepared according to the method of the present invention, an experiment was carried out by the following method. As a GC analysis, TE90 carbon composition analysis was performed.

After the transesterification reactions according to Examples 1-6 and Comparative Examples 1-4, the contents of glycerin and unconverted glycerides were measured using a gas chromatography (GC analysis). The content results of glycerin and glycerides after the first transesterification reaction and after the completion of the second transesterification reaction in Examples were shown in Table 2 below.

TABLE 2

| | | (Unit: based on wt. %) | | | | |
| --- | --- | --- | --- | --- | --- | --- |
| | Trans-esterification Reaction | Content of Glycerin | Content of Monoglyceride | Content of Diglyceride | Content of Triglyceride | Total Amount |
| Ex. 1 | Step 1 | 1.2 | 1.1 | 8.8 | 42.2 | 53.3 |
| | Step 2 | 0.4 | 0.9 | 0.7 | 0.4 | 2.4 |
| Ex. 2 | Step 1 | 1.2 | 2.1 | 9.8 | 43.2 | 56.6 |
| | Step 2 | 0.9 | 1.1 | 1.4 | 0.8 | 4.2 |
| Ex. 3 | Step 1 | 1.2 | 0.7 | 8.0 | 41.2 | 51.1 |
| | Step 2 | 0.2 | 0.9 | 0.5 | 0.2 | 1.8 |
| Ex. 4 | Step 1 | 1.2 | 1.5 | 8.8 | 42.6 | 54.1 |
| | Step 2 | 0.4 | 0.9 | 0.8 | 0.4 | 2.5 |
| Ex. 5 | Step 1 | 22 | 1.1 | 8.8 | 43.2 | 55.3 |
| | Step 2 | 0.4 | 0.9 | 0.7 | 0.3 | 2.3 |
| Ex. 6 | Step 1 | 1.2 | 1.1 | 8.8 | 42.2 | 53.3 |
| | Step 2 | 0.4 | 0.9 | 0.7 | 0.4 | 2.4 |
| Com. Ex. 1 | | 1.5 | 1.5 | 9.0 | 43.5 | 55.5 |
| Com. Ex. 2 | | 1.5 | 1.5 | 9.0 | 45.0 | 57.0 |
| Com. Ex. 3 | | 1.0 | 1.1 | 8.6 | 41.8 | 52.5 |
| Com. Ex. 4 | | 1.2 | 1.1 | 8.8 | 42.2 | 53.3 |

As seen in Table 2 above, the fabric softeners in Examples 1-6 prepared by the method according to the present invention exhibited glycerin and unconverted glycerides in 1.8-4.2 wt. %, so that they have higher conversion rate of glycerides than 52.5-57.0 wt. % of Comparative Examples 1-4. Moreover, when fabric softeners were prepared in Comparative Examples, their stability was not good because of high oily components due to the high contents of glycerin and glycerides.

Experimental Example 3

Test Evaluation of Fabric Softener

Fabric softeners were manufactured by adding 7% of the esterquats prepared in Example 1 and Comparative Example 1. The manufactured fabric softeners were evaluated with regard to the following items by Korea Apparel Testing & Research Institute.

TABLE 3

| Test Items | What performances can be expected from softeners? |
|---|---|
| Triboelectrification | Evaluating whether static occurrence due to the friction of fabric products can be reduced by the treatment of softeners. KS K 0555 B:2005 |
| Stiffness Test (Drape Property) | Referring to the degree of softness. As it gets softer, it droops down more due to its weight. Numerical evaluation on how soft fabric products which got stiff by laundry can become by softeners. KS K 0815 6.21 e)-2008 |
| Absorption Test | Testing on how well softener-treated fabrics can absorb water. A good softener can make fabrics soft and also make them absorb water well. KS K 0851 6.27.1 b-2008 |
| Tactility Test | Overall senses people feel when they touch apparels. Evaluated by panels' direct touch on how soft and flufy tactility the fabric products which become rough by synthetic detergents can have by softeners. Evaluated by 15 panels after touching softener-treated specimens with their hands. |

TABLE 4

| Measurement Items | | Com. Ex. 1 | Ex. 1 |
|---|---|---|---|
| Solid Content (%) | | 6.26 | 6.17 |
| Triboelectrification (V) | Cotton Rubbing Cloth | 1800 | 1400 |
| | Wool Rubbing Cloth | 3700 | 2700 |
| | Average | 2750 | 2050 |
| Stiffness (Drape scale) | | 0.482 | 0.465 |
| Absorption (mm) | Warp | 39 | 41 |
| | Wept | 37 | 38 |
| | Average | 38 | 39.5 |
| Tactility Test Result | | 2.2 | 1.1 |

When a fabric softener containing an esterquat is prepared by the method according to the present invention, the content of unconverted glyceride, glycerylester or a combination thereof can be reduced and a fabric softener with excellent long-term stability can be produced.

The invention claimed is:

1. A method of preparing an esterquat of Formula 1 in a fabric softener,

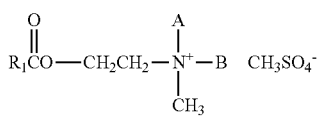

[Formula 1]

wherein A and B are each independently $CH_2CH_2OH$ or $CH_2CH_2OCR_2$, and $R_1$ and $R_2$ are each independently selected from the group consisting of a linear or branched alkyl group and alkenyl group of $C_1$-$C_{21}$, and a combination group thereof, the method comprising:

performing a first esterification reaction of a fatty acid containing triglyceride oil and a tertiary hydroxyalkylamine in a reactor at a temperature of 110-130° C. under the pressure condition of 50 mmHg or less;

performing a second esterification reaction at a temperature of 130-160° C. at a point where 40-60% of the triglyceride oil is converted into a fatty acid hydroxyalkylamine ester; and performing a quaternization reaction by reacting said fatty acid hydroxyalkylamine ester with a quaternizing agent in a solvent to prepare the esterquat of Formula 1 above, wherein said fabric softener includes at least one material selected from the group consisting of glycerin and glycerides represented by formulae 2 to 6 below in an amount of 0.001 to 5 wt. %, and

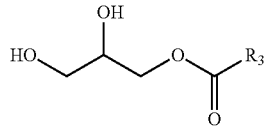

[Formula 2]

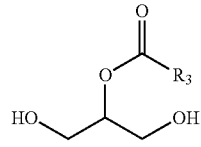

[Formula 3]

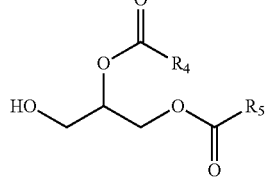

[Formula 4]

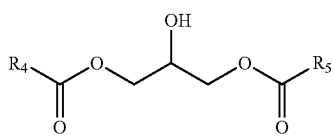

[Formula 5]

[Formula 6]

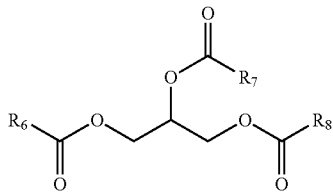

wherein R₃ to R₈ are each independently a linear or branched alkyl group or alkenyl group of $C_{11}$-$C_{21}$.

2. The method of preparing an esterquat of Formula 1 in a fabric softener according to claim 1, wherein the reactor is a closed reactor connected with a reduced pressure pump and a glycerin reservoir.

3. The method of preparing an esterquat of Formula 1 in a fabric softener according to claim 2, wherein a glycerin produced in the reaction is discharged to the outside of the reactor and then transferred to the reservoir.

4. The method of preparing an esterquat of Formula 1 in a fabric softener according to claim 1, wherein the second esterification reaction is performed under a lower pressure than that of the first esterification reaction.

5. The method of preparing an esterquat of Formula 1 in a fabric softener according to claim 1, wherein the pressure of the first esterification reaction is 10 to 50 mmHg, and the pressure of the second esterification reaction is 0 to 10 mmHg.

6. The method of preparing an esterquat of Formula 1 in a fabric softener according to claim 1, wherein the first esterification reaction is performed for 3 to 10 hours, and the second esterification reaction is performed for 1 to 13 hours.

7. The method of preparing an esterquat of Formula 1 in a fabric softener according to claim 1, wherein a catalyst for the esterification is at least one selected from the group consisting of sodium alkoxide catalysts, titanium oxide catalysts, zinc oxide catalysts, silica, alkali catalysts, sodium hypochlorite, and a combination thereof.

8. The method of preparing an esterquat of Formula 1 in a fabric softener according to claim 7, wherein the catalyst is used in an amount of 0.01 to 0.1 parts by weight with regard to a total of 100 parts by weight of the fatty acid containing triglyceride oil and the tertiary hydroxyalkylamine.

9. The method of preparing an esterquat of Formula 1 in a fabric softener according to claim 1, wherein the triglyceride oil is selected from the group consisting of a palm oil, palm stearin oil, palm olein oil, coconut oil, olive oil, soybean oil, and a combination thereof.

10. The method of preparing an esterquat of Formula 1 in a fabric softener according to claim 1, wherein the tertiary hydroxyalkylamine is selected from the group consisting of diethanol/methylamine, 1,2-dihydroxypropyl dimethylamine, triethanolamine, and a combination thereof.

11. The method of preparing an esterquat of Formula 1 in a fabric softener according to claim 1, wherein the solvent is selected from the group consisting of a lower alcohol having carbon atoms of 1 to 6, alkylene glycol having carbon atoms of 1 to 6, glycerin and a combination thereof.

12. The method of preparing an esterquat of Formula 1 in a fabric softener according to claim 11, wherein the glycerin is recovered from the esterification reaction.

* * * * *